United States Patent [19]

Behnke et al.

[11] 4,123,609

[45] Oct. 31, 1978

[54] PROCESS FOR THE PRODUCTION OF 9-(β-D-ARABINOFURANOSYL)ADENINE, 5'-PHOSPHATE

[75] Inventors: Walter E. Behnke, St. Clair Shores; William R. Marsh, Roseville; Theodore H. Haskell, Ann Arbor, all of Mich.

[73] Assignee: Warner-Lambert Company, Morris Plains, N.J.

[21] Appl. No.: 831,703

[22] Filed: Sep. 12, 1977

Related U.S. Application Data

[63] Continuation-in-part of Ser. No. 738,425, Nov. 3, 1976, abandoned.

[51] Int. Cl.$^2$ ............................................. C07H 17/00
[52] U.S. Cl. ....................................... 536/27; 536/28; 536/29
[58] Field of Search ................................... 536/27, 28

[56] References Cited

U.S. PATENT DOCUMENTS

| | | | |
|---|---|---|---|
| 3,413,282 | 11/1968 | Yoshikawa et al. | 536/27 |
| 3,919,194 | 11/1975 | Kikugawa et al. | 536/27 |

*Primary Examiner*—Johnnie R. Brown
*Assistant Examiner*—Blondel Hazel
*Attorney, Agent, or Firm*—David B. Ehrlinger; Stephen Raines; Frank S. Chow

[57] ABSTRACT

Process for the production of an ester product, 9-(β-D-arabinofuranosyl)adenine, 5'-phosphate, in which the mixture resulting from reaction of 9-(β-D-arabinofuranosyl)adenine with phosphorylating agent in trialkyl phosphate solvent is subjected to aqueous hydrolysis, the pH of the hydrolysis mixture is adjusted upward sufficiently to cause separation into aqueous and non-aqueous liquid phases, the trialkyl phosphate solvent is removed, and the product is precipitated from the residual aqueous mixture and isolated.

15 Claims, No Drawings

PROCESS FOR THE PRODUCTION OF 9-(β-D-ARABINOFURANOSYL)ADENINE, 5'-PHOSPHATE

This application is a continuation-in-part of U.S. Pat. application Ser. No. 738,425 filed Nov. 3, 1976 and now abandoned.

SUMMARY AND DETAILED DESCRIPTION

The present invention relates to a process for the production of the ester product, 9-(β-D-arabinofuranosyl)adenine, 5'-phosphate, by phosphorylation of 9-(β-D-arabinofuranosyl)adenine and hydrolysis of the phosphorylated product. More particularly, the invention relates to such process in which the desired ester product is obtained in crystalline form directly from the reaction mixture.

In one prior art method for preparing the 5'-phosphate ester of a nucleoside (U.S. Pat. No. 3,703,507), the corresponding nucleoside is reacted with phosphorus oxychloride ($POCl_3$) in acetic acid in the presence of pyridine. In another prior art method (U.S. Pat. No. 3,413,282), the corresponding nucleoside is reacted with $POCl_3$ or diphosphoryl chloride ($P_2O_3Cl_4$) in the presence of trialkyl phosphate solvent, the reaction product is hydrolyzed and neutralized, and the desired nucleotide product is isolated by adsorption and elution techniques using activated carbon or ion exchange resin. The prior art methods undesirably involve time-consuming manipulations and processing steps; they also use costly adsorbing media and elution solvents.

The present invention, in a process for the production of the ester product 9-(β-D-arabinofuranosyl)adenine, 5'-phosphate, comprises the steps of reacting 9-(β-D-arabinofuranoxyl)adenine with a phosphorylating agent in the presence of trialkyl phosphate solvent, subjecting the reaction mixture to aqueous hydrolysis, adjusting the pH of the aqueous hydrolysis mixture upward sufficiently to cause separation into aqueous and non-aqueous liquid phases, removing the trialkyl phosphate solvent from the aqueous mixture, maintaining the residual aqueous mixture at a pH at which the ester product is insoluble to cause said ester product to precipitate as a solid phase from the aqueous mixture, and isolating said product. The process of the invention advantageously provides good yields of the desired product in crystalline form. The process also provides a favorable ratio of required volume to product yield thereby permitting increased batch sizes; the product work-up is simple, and labor and material needs are minimized.

The process of the invention is subject to considerable variation. The starting material, 9-(β-D-arabinofuranosyl)adenine can be used either as the monohydrate or in the anhydrous form, the anhydrous nucleoside being preferred. The phosphorylating agent employed is any suitable agent such as a phosphorous oxyhalide, in particular $POCl_3$, $POBr_3$ and $P_2O_3Cl_4$. The phosphorylating agent is used in a ratio of about 1 to 5 moles, and preferably about 1.15 to 2 moles, for each mole of 9-(β-D-arabinofuranosyl)adenine. Phosphorus oxychloride is a preferred phosphorylating agent. The trialkyl phosphate solvent used is an ester of phosphoric acid with a $C_1$ to $C_4$ aliphatic alcohol, such as trimethyl phosphate or triethyl phosphate. Triethyl phosphate is a preferred solvent. The molar ratio of trialkyl phosphate solvent to nucleoside in the process is at least 5 to 1. A ratio of about 15 to 1 is preferred for best results. The phosphorylation is ordinarily carried out at temperatures from −30° to 50° C. The preferred range is between −10° to +10° C. at which the reaction is complete in about 2 to 5 hours. At −20° C. the reaction time is about 6 to 10 hours and at 30° C. about 10 to 30 minutes. Following the reaction, the phosphorodihalidate or trichlorodiphosphate intermediate is hydrolyzed to provide the ester product. This can be done by combining ice and/or water with the reaction mixture. The pH of the resulting aqueous mixture is according to the invention adjusted upwardly by addition of base such as sodium hydroxide solution in sufficient amount to cause separation into an aqueous liquid phase and a non-aqueous liquid phase, suitably to a value in the pH range from about 1 to about 2.5 or higher. The resulting mixture, which forms the two liquid phases, is extracted with an inert water-immiscible solvent such as dichloromethane or diethyl ether to remove the trialkyl phosphate. Since the desired product, 9-(β-D-arabinofuranosyl)adenine, 5'-phosphate, is water-soluble at relatively low pH and at relatively high pH, the extracted aqueous phase is maintained according to the invention, if necessary after further adjustment, at a pH at which the product is insoluble (depending on conditions suitably in the pH range from about 1.3 to about 2.5) and the mixture is held, preferably in the cold and with seeding, to cause the desired ester product to precipitate as a solid phase from the aqueous mixture. The product, obtained in pure crystalline form, is isolated in free acid form by conventional means such as filtration or centrifugation. The product can be recrystallized, if desired, or converted to salt form in solution by conventional means, for example, by appropriate adjustment of the pH. In an optional procedure, instead of hydrolyzing the reaction mixture directly in water as described, one can hydrolyze the intermediate phosphorodihalidate or trichlorodiphosphate precipitate obtained by adding the reaction mixture to a non-aqueous liquid (such as dichloromethane or diethyl ether) in which the intermediate is insoluble.

The product, 9-(β-D-arabinofuranosyl)adenine, 5'-phosphate, is useful as a pharmacological agent, especially as an antiviral agent, being active against Herpes simplex virus, as described in the above-mentioned U.S. Pat. No. 3,703,507, which description is incorporated herein by reference.

The invention is illustrated by the following examples.

EXAMPLE 1

A stirred mixture of 10.69 g. (0.04 mole) of anhydrous 9-(β-D-arabinofuranosyl)adenine in 100 ml. (0.586 mole) of triethyl phosphate was cooled to 0°–2° C. in an ice bath. To this stirred slurry was then added 7.05 g. (0.046 mole) of phosphorus oxychloride dropwise during a two hour period while maintaining ice bath cooling. The mixture was then stirred cold for another hour to give a clear to slightly hazy solution which was poured onto 70 g. of ice. The reaction flask was rinsed with 10 ml. of ice water and this was added to the hydrolysis mixture which was then stirred in an ice bath for about 15 minutes. The mixture was stirred with cooling while the pH was adjusted from 0.6 to 2 using 50% sodium hydroxide solution. A second liquid phase separated and the temperature rose to about 10° C. during this step. The mixture was stirred for another 15 minutes while the pH was held at 2 by the addition of more base.

The mixture was then transferred to a separatory funnel and extracted with 100 ml. of dichloromethane. The lower phase (non-aqueous, about 200 ml.) was removed and the aqueous layer was again extracted using 50 ml. of dichloromethane. The layers were again separated and the upper (aqueous) phase was readjusted to pH 2 using a few drops of base. This solution was seeded with a few crystals of 9-(β-D-arabinofuranosyl)adenine, 5'-phosphate, and stirred at room temperature until precipitation was well underway (about 10 minutes). Stirring was then stopped and the mixture was allowed to stand in the cold overnight. The resulting white crystalline mass was broken up by stirring and again allowed to stand overnight in the cold. The mixture was then filtered with suction, and the crystalline product, 9-(β-D-arabinofuranosyl)adenine, 5'-phosphate, was washed successively with ice water (22 ml.), cold 50% aqueous ethanol (35 ml.), and cold absolute ethanol (25 ml.). After drying at 40° C. in vacuo for 16 hours the product weighed 10.59 g. (76.2% of theory) and analyzed as follows:

| Ion Exchange Column Chromatography - UV Assay: | |
| --- | --- |
| Fraction I (unreacted nucleoside + adenine): | 1.57% |
| Fraction II (desired 5'-phosphate product): | 91.2% |
| Fraction III (diphosphates): | 1.98% |
| K. Fisher Water: | 5.62% |
| Total = | 100.37% |

The corrected yield of 9-(β-D-arabinofuranosyl)adenine, 5'-phosphate was therefore 69.5% of theory.

The product analysis is carried out by the following procedure which is typical:

Ion Exchange Column Chromatography - UV Assay

A chromatographic column (9 mm. × 15 cm.) is packed with 0.5 g. of anion exchange resin (QAE-Sephadex A-25, Cl$^-$) which has been suspended in distilled water overnight. Approximately 20 mg. of sample is accurately weighed and dissolved in 1.0 ml. of 0.1N NaOH and this solution is transferred to the column. The column is then eluted with water until a total of 25 ml. has been collected in a volumetric flask. This fraction contains unreacted 9-(β-D-arabinofuranosyl)adenine and adenine. The column is then eluted with 0.1M phosphate buffer (pH 7.0) until 50 ml. has been collected. This second fraction contains the desired 5'-phosphate product. A third fraction containing diphosphate esters is obtained by eluting with 0.4M phosphate buffer (pH 7.0) until a total of 50 ml. has been collected.

The UV spectrum of each fraction is run at 320–220 nm. (Fractions 1 and 3 without dilution and fraction 2 after a 20-fold dilution). From the absorption at 260 nm. ($A_{\lambda 260}$), the contents of each fraction are calculated as follows:

$$\text{mg. of component} = \frac{A_{\lambda 260}}{a\,(1\%,\,1\,\text{cm.})_{\lambda 260}} \times 10 \times V \times D$$

where
$V$ = volume (ml.) of each fraction
$D$ = dilution
$a\,(1\%,\,1\,\text{cm.})_{\lambda 260}$ = 569 for 9-(β-D-arabinofuranosyl)adenine (Fraction I)
 = 437 for the 5'-phosphate product (Fraction II)
 = 361 for the diphosphates (Fraction III)

From the amount of each component, the percent of each is then calculated.

EXAMPLE 2

To 100 ml. of stirred, cold (2° C.) triethyl phosphate was added 9.20 g. (0.06 mole) of phosphorus oxychloride within a two minute period. To this stirred solution was then added 10.69 g. (0.04 mole) of anhydrous 9-(β-D-arabinofuranosyl)adenine in one portion with a resultant reaction temperature rise to about 4° C. The mixture was stirred in the ice bath for 2 hours 10 minutes, producing a clear solution about 1 hour 50 minutes after the addition. The reaction solution was then poured into 800 ml. of cold diethyl ether and stirred for one hour in an ice bath. This white suspension was filtered in the cold and the hygroscopic solid was washed twice with 100-ml. portions of cold solvent, then dissolved in 80 ml. of water. After separating an ether layer, the aqueous solution was adjusted to pH 2 using 50% sodium hydroxide solution, then seeded with pure 9-(β-D-arabinofuranosyl)adenine, 5'-phosphate, and placed in the refrigerator to cool for two days with occasional stirring. The precipitate was then filtered, washed in turn with 35 ml. of cold 50% ethanol and 25 ml. of cold absolute ethanol, and finally, dried in vacuo at 40° C. to give 8.88 g. (63.9% of theory) of 9-(β-D-arabinofuranosyl)adenine, 5'-phosphate, assaying as follows:

| Ion Exchange Column Chromatography - UV assay: | |
| --- | --- |
| Fraction I (unreacted nucleoside + adenine): | 0.38% |
| Fraction II (desired 5'-phosphate product): | 92.8% |
| Fraction III (diphosphates): | 4.03% |

The corrected yield of 9-(β-D-arabinofuranosyl)adenine, 5'-phosphate, was therefore 59.3% of theory.

EXAMPLE 3

To 100 ml. of triethyl phosphate was added 10.69 g. (0.04 mole) of anhydrous 9-(β-D-arabinofuranosyl)adenine in one portion with stirring. This mixture was cooled in an ice bath to 2° C. and 9.20 g. (0.06 mole) of phosphorus oxychloride was then added during a three-minute period, the temperature rising to about 4° C. The reaction mixture was stirred in the cold for 2 hours 30 minutes, after which the clear solution was poured into 80 g. of ice. This mixture was stirred in an ice bath to maintain a temperature below 10° C. while the pH was adjusted to 2 using 50% sodium hydroxide solution. The resulting turbid mixture was extracted twice using 100-ml. and 50-ml. portions of dichloromethane and the aqueous layer was again adjusted to pH 2 using additional caustic. After seeding, this solution was placed in the refrigerator overnight to give a dense white precipitate. This was stirred with a glass rod and again allowed to stand overnight in the cold. The white product was filtered and washed using 22 ml. of ice water, 35 ml. of cold 50% ethanol and 25 ml. of cold absolute ethanol. After drying in vacuo at 40° C., 9.60 g. (69.1% of theory) of the product, 9-(β-D-arabinofuranosyl)adenine, 5'-phosphate, was obtained which assayed as follows:

| Ion Exchange Column Chromatography - UV assay: | |
| --- | --- |
| Fraction I (unreacted nucleoside + adenine): | 0.17% |
| Fraction II (desired 5'-phosphate product): | 89.9% |
| Fraction III (diphosphates): | 4.54% |

The corrected yield of 9-(β-D-arabinofuranosyl)adenine, 5'-phosphate was therefore 62.1% of theory.

EXAMPLE 4

To an ice bath-cooled solution of 0.72 ml. (0.04 mole) of water in 100 ml. of triethyl phosphate was slowly added 12.27 g. (0.08 mole) of phosphorus oxychloride at 0°–5° C. Anhydrous 9-(β-D-arabinofuranosyl)adenine (10.69 g., 0.04 mole) was then added in one portion with stirring to give an immediate temperature rise from 1° to 9° C. The reaction mixture was clear in 30 minutes and after 2 hours 30 minutes it was poured onto 100 g. of ice and the pH was adjusted to 2 using 50% sodium hydroxide solution. After extracting twice using 200-ml. and 100-ml. portions of diethyl ether, the pH was again adjusted using additional base. The aqueous solution was then seeded with crystals of 9-(β-D-arabinofuranosyl)adenine 5'-phosphate, and cooled in the refrigerator to precipitate the product, 9-(β-D-arabinofuranosyl)adenine, 5'-phosphate, as described in previous examples. After filtering, washing, and drying, the white product weighed 10.12 g. (72.9% of theory) and assayed as follows:

| Ion Exchange Column Chromatography - UV Assay: | |
|---|---|
| Fraction I (unreacted nucleoside + adenine): | 4.08% |
| Fraction II (desired 5'-phosphate product): | 81.1% |
| Fraction III (diphosphates): | 1.51% |

The corrected yield of 9-(β-D-arabinofuranosyl)adenine, 5'-phosphate, was 59.1%.

EXAMPLE 5

To a stirred slurry of 10.69 g. (0.04 mole) of 9-(β-D-arabinofuranosyl)adenine in 100 ml. of triethylphosphate cooled to 2° C. in an ice bath was added during a 2-hour period 11.58 g. (0.046 mole) of diphosphoryl chloride ($P_2O_3Cl_4$). The white reaction mixture was stirred in the cold for an additional hour, becoming a clear solution during this time. This solution was then poured onto 80 g. of ice and 50% sodium hydroxide solution was added to this stirred, ice bath-cooled mixture to adjust the pH to 2. After extracting with dichloromethane, readjusting the pH and seeding, the aqueous solution was cooled. The product which separated as a white crystalline solid, 9-(β-D-arabinofuranosyl)adenine, 5'-phosphate, was collected by filtration and washed and dried, as described in previous examples to give 8.26 g. (59.5% of theory) which assayed as follows:

| Ion Exchange Column Chromatography - UV Assay: | |
|---|---|
| Fraction I (unreacted nucleoside + adenine): | 0.24% |
| Fraction II (desired 5'-phosphate product): | 94.3% |
| Fraction III (diphosphates): | 2.0% |
| K. Fisher Water: | 5.77% |
| Total = | 102.3% |

The corrected yield of 9-(β-D-arabinofuranosyl)adenine, 5'-phosphate was therefore 56.1% of theory.

We claim:

1. In a process for the production of the ester product 9-(β-D-arabinofuranosyl)adenine, 5'-phosphate, comprising converting 9-(β-D-arabinofuranosyl)adenine to a 5'-monophosphorylated intermediate product in the presence of trialkyl phosphate solvent, and subjecting the reaction mixture to aqueous hydrolysis, the steps of isolating the ester product in crystalline form by means other than adsorption and elution comprising adjusting the pH of the aqueous hydrolysis mixture upward sufficiently to cause separation into aqueous and non-aqueous liquid phases, removing the trialkyl phosphate solvent from the aqueous mixture, maintaining the residual aqueous mixture at a pH at which the ester product is insoluble to cause said ester product to precipitate directly in crystalline form from the aqueous mixture, and isolating said crystalline ester product.

2. In a process for the production of the ester product 9-(β-D-arabinofuranosyl)adenine, 5'-phosphate, comprising converting 9-(β-D-arabinofuranosyl)adenine to a 5'-monophosphorylated intermediate product in the presence of trialkyl phosphate solvent, treating the reaction mixture with a non-aqueous diluent in which the intermediate product is insoluble to cause said intermediate product to separate as a solid, isolating the solid and subjecting it to aqueous hydrolysis, the steps of isolating the ester product in crystalline form by means other than adsorption and elution comprising maintaining the aqueous hydrolysis mixture at a pH at which the ester product is insoluble to cause said ester product to precipitate directly in crystalline form from the aqueous mixture, and isolating said crystalline ester product.

3. Process according to claim 1 in which the phosphorylating agent is used in a ratio of 1.15 to 2 moles for each mole of 9-(β-D-arabinofuranosyl)adenine.

4. Process according to claim 1 in which the phosphorylating agent is phosphorous oxychloride.

5. Process according to claim 1 in which the solvent is triethyl phosphate.

6. Process according to claim 1 in which the molar ratio of triakyl phosphate to 9-(β-D-arabinofuranosyl)adenine is about 15 to 1.

7. Process according to claim 1 in which the phosphorylation is carried out at temperatures between $-10°$ to $+10°$ C.

8. Process according to claim 1 in which the aqueous hydrolysis mixture is adjusted to a pH in the range from about 1 to about 2.5.

9. Process according to claim 1 in which the residual aqueous mixture is maintained at a pH in the range from about 1.3 to about 2.5.

10. Process according to claim 2 in which the phosphorylating agent is used in a ratio of 1.15 to 2 moles for each mole of 9-(β-D-arabinofuranosyl)adenine.

11. Process according to claim 2 in which the phosphorylating agent is phosphorous oxychloride.

12. Process according to claim 2 in which the solvent is triethyl phosphate.

13. Process according to claim 2 in which the molar ratio of triakyl phosphate to 9-(β-D-arabinofuranosyl)adenine is about 15 to 1.

14. Process according to claim 2 in which the phosphorylation is carried out at temperatures between $-10°$ to $+10°$ C.

15. Process according to claim 2 in which the aqueous hydrolysis mixture is maintained at a pH in the range from about 1.3 to about 2.5.

* * * * *